United States Patent [19]

Takahashi et al.

[11] 4,036,984
[45] July 19, 1977

[54] SOIL FUNGI INHIBITING AGENT

[75] Inventors: Hiroki Takahashi; Kiyomi Ozawa; Yoshihiro Iwasawa, all of Funabashi; Masayuki Ogawa, Minami; Shigekatu Okamoto, Minami; Yoshinori Ochiai, Minami; Eizo Katakura, Minami, all of Japan

[73] Assignee: Nissan Chemical Industries, Ltd., Tokyo, Japan

[21] Appl. No.: 571,925

[22] Filed: Apr. 28, 1975

[30] Foreign Application Priority Data

Apr. 30, 1974 Japan .................... 49-048420
Mar. 15, 1975 Japan .................... 50-031416

[51] Int. Cl.$^2$ ............................ A01N 9/24
[52] U.S. Cl. ................. 424/311; 424/267; 424/301; 424/305; 424/308; 424/309; 424/312; 424/314
[58] Field of Search .......... 424/311, 312, 314; 260/488 CD

[56] References Cited

U.S. PATENT DOCUMENTS

| | | | |
|---|---|---|---|
| 1,804,503 | 5/1931 | Gardner | 260/488 CD |
| 1,841,430 | 1/1932 | Bollmann | 260/488 CD |
| 2,344,491 | 3/1944 | Britton et al. | 260/488 CD |
| 2,620,359 | 12/1952 | Britton et al. | 260/488 CD |
| 2,765,224 | 10/1956 | Cambrech | 260/488 CD |

Primary Examiner—Leonard Schenkman
Attorney, Agent, or Firm—Brisebois & Kruger

[57] ABSTRACT

Soil fungi-inhibiting agent containing as the active ingredient one or more of the compounds represented by the following general formula

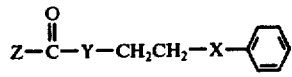

wherein
i. when both X and Y are oxygen atoms, Z is hydrogen atom, unsubstituted alkyl group, unsubstituted alkenyl group,

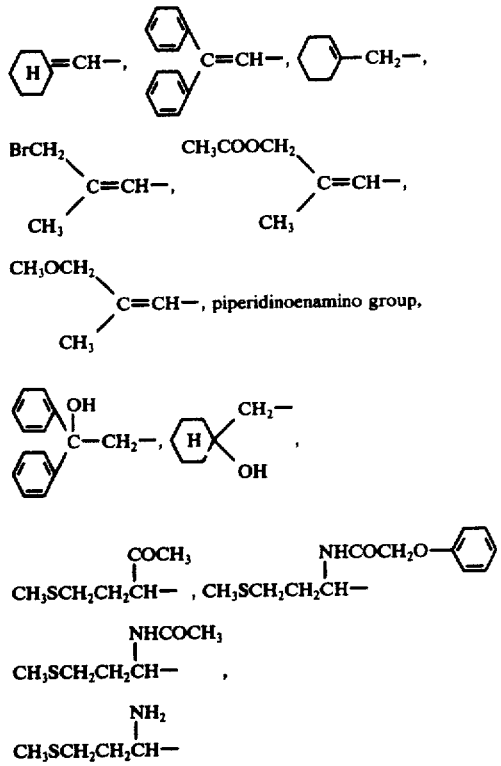

(in this case the compound is p-toluene sulfonate), $NH_2CH_2$— (in this case the compound is p-toluene sulfonate), acyl group, $ClCH_2CONH$—, or alkyl group substituted by substituents such as $R_1COO$—, $CH_3COS$—, $R_2O$—, $R_2S$—, $HO$—, $HOOC$—, $CH_3CONH$—, acyl group, alkoxyacyl group, where $R_1$ is lower-alkyl group or alkenyl group, $R_2$ is lower-alkyl group or benzyl group;

ii. when X is oxygen and Y is sulfur or —NH—, Z is lower alkyl group;

iii. when X is sulfur and Y is oxygen, Z is lower-alkyl group, acetylmethyl group, methoxymethyl group, 2-methyl-1-propynyl group or nitromethyl group;

iv. when X is sulfur and Y is —NH—, Z is lower-alkyl group.

8 Claims, No Drawings

SOIL FUNGI INHIBITING AGENT

DETAILED DESCRIPTION OF THE INVENTION

The present invention relates to a soil fungi-inhibiting agent, more specifically to a soil fungi-inhibiting agent containing as the active ingredient one or more of the compounds represented by the following general formula I:

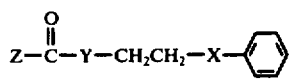
(I)

wherein
i. when both X and Y are oxygen atoms, Z is hydrogen atom, unsubstituted alkyl group, unsubstituted alkenyl group,

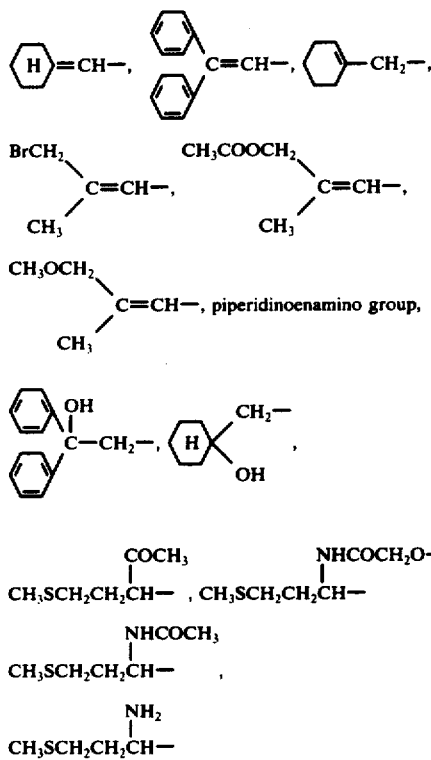

(in this case the compound is p-toluene sulfonate), $NH_2CH_2-$ (in this case the compound is p-toluene sulfonate), acyl group, $ClCH_2CONH-$, or alkyl group substituted by substituents such as $R_1COO-$, $CH_3COS-$, $R_2O-$, $R_2S-$, $HO-$, $HOOC-$, $CH_3CONH-$, acyl group, alkoxyacyl group, where $R_1$ is lower-alkyl group or alkenyl group, $R_2$ is lower-alkyl group or benzyl group;

ii. when X is oxygen and Y is sulfur or $-NH-$, Z is lower alkyl group;

iii. when X is sulfur and Y is oxygen, Z is lower-alkyl group, acetylmethyl group, methoxymethyl group, 2-methyl-1-propynyl group or nitromethyl group;

iv. when X is sulfur atom and Y is $-NH-$, Z is lower-alkyl group.

Inhibition of soil fungi has been extremely difficult and various chemicals have been tested for this purpose, but no fully satisfactory effect has been obtained from commercially available chemicals. Thus, the discovery of a fully satisfactory soil fungicide is strongly being demanded by people engaged in agriculture and horticulture. No fully satisfactory soil fungi-inhibiting agent is available on the market; some chemcials are strong in fungicidal power but give phyto-toxicities to the crop; some cannot be sufficiently fungicidal unless applied in high concentrations; some are toxic to humans and animals; and some are irritating, corrosive to metals or give off a bad odor. Chloropicrin, which is now marketed, has, in addition to the above-mentioned demerits, the following disadvantages: To effectively inhibit the soil fungi, about 30kg of chloropicrin has to be applied per 10 are; moreover, degassing of it takes several weeks before the sowing of the crop; and the crop cannot be sown before this can be completed.

After testing of many compounds to develop a soil fungi-inhibiting agent which does not give phyto-toxcities on the crop or is not toxic to humans and animals, the present inventors have accomplished the present invention through discovery that compounds represented by the above-mentioned general formula are effective for killing soil fungi and especially effective for controlling damage due to Fusarium.

The compounds according to the present invention are weakly fungicidal to Fusarium, i.e., a typical soil fungus, but they are extremely effective for protecting the crop from damage due to the soil fungi. Since they have no phyto-toxicities on the crop, they can be applied to the soil at the same time as the crop is sown, which is a great advantage.

All the compounds according to the present invention can be easily synthesized by known methods from materials which can easily be obtained industrially.

The following are non-restrictive examples illustrating the synthesis of the compounds according to the present invention.

EXAMPLE 1

β-phenoxyethyl pentadecanoate (Compound No. 18)

Pentadecanoic acid (24.2g) was treated with thionyl chloride (13.1g) at 80°-90° C. Pentadecanoyl chloride, thus obtained, was added slowly under ice cooling into the mixture of β-phenoxyethylalcohol (13.8g), pyridine (10.3g) and benzene (100ml) with stirring. After having been stirred, the reaction mixture was treated with an ordinary method (washed with dilute hydrochloric acid, the benzene layer was dried over Glauber's salt, and then benzene was removed under reduced pressure, giving a crude product). Solid (33g) was obtained. The solid was recrystalized from n-hexane, from which it formed colourless crystals (26g), m.p. 45.0°–47.0° C, of β-phenoxyethyl pentadecanoate.

EXAMPLE 2

β-phenoxyethylacrylate (Compound No. 23)

This compound was prepared according to a known process (Chemical Abstracts Vol. 59,11323[9]). Namely, acrylic acid-chloride (5g) was added slowly under ice cooling into the mixture of β-phenoxyethylalcohol (6.75g), sodium-carbonate (2.9g), cuprous chloride (0.2g) and benzene (50ml) with stirring. The mixture was allowed to stand 15 hours at room temperature and then refluxed for 4 hours. The rection mixture was treated according to the above mentioned known process, giving a crude product (6.6g).

The crude product on fractionation gave a fraction (4.7g), b.p. 88.0° C/0.1mmHg, of β-phenoxy-ethyl acrylate.

EXAMPLE 3

β-phenoxyethyl crotonate (Compound No. 24)

Crotonyl chloride (5.3g) was added slowly under ice cooling into the mixture of β-phenoxyethylalcohol (6.9g), pyridine (4.7g) and benzene (100ml) with stirring and the stirring was continued for another 4 hours at room temperature.

A crude prouduct, obtained according to an ordinary method, on fractionation gave a fraction (3.7g), b.p. 96.0° C/0.11mmHg-97.0° C/0.12mmHg, of β-phenoxyethyl crotonate.

EXAMPLE 4

β-phenoxyethyl 3-methyl-2-pentenoate (Compound No. 25)

In a dry-reaction flask fitted with a mechanical stirrer, separatory funnel, and a refluxing condenser, was placed granulated zinc (65.4g). A solution of methyl-ethyl ketone (72g) and ethyl bromoacetate (167g) in benzene (500ml) and toluene (500ml) was placed in the separatory funnel. About 50ml of this solution was added to the zinc and the flask was warmed until the reaction started. The mixture was then stirred and the rest of the solution introduced at such a rate that gentle refluxing occurred. Refluxing was continued for an additional 5 hours. The flask was then cooled and the contents poured into a sulfuric acid solution consisting of concentrated sulfuric acid (85ml) and water (1500ml) under ice cooling. The acid layer was drawn off and the organic layer was dried over Grauber's salt, concentrated. giving 3-hydroxy-3-methyl-pentanoate (126g).

This product was added slowly, about one half hour being required, under ice cooling to a solution of potassium hydroxide (65.8g) in water (70ml) and methylalcohol (1300ml) and the stirring was continued for another 2.5 hours at room temperature. Methyl alcohol and water were removed under reduced pressure and water (120ml) was added to the residue, neutralized with dilute hydrochloric acid, extracted with ethylether, and the ether extract was dried, and concentrated, giving 3-hydroxy-3-methylpentanoic acid (67.7g). This compound (67.7g) was refluxed in acetic anhydride (210g) for 3 hours.

Excess acetic anhydride and yielded acetic acid were removed under reduced pressure and thus 3-methylpentene-2-acid (58.3g) was obtained. This was chlorinated with thionyl chloride (85.5g) at 80°-100° C, giving 3-methyl-pente-2-noyl chloride, b.p. 84.8°-85.5° C/48mmHg. This product was treated with β-phenoxyethyl alcohol as the same method in Example 3, giving β-phenoxyethyl 3-methyl-2-pentenoate, b.p. 104.0°-105.0° C/0.035mmHg.

EXAMPLE 5

β-phenoxyethyl-3-hydroxy-3-methyl-pentanoate (Compound No. 38)

This compound was prepared by the same method as described above. β-phenoxyethyl bromoacetate (256g) was used in place of the ethyl bromoacetate used in Example 4. β-phenoxyethyl-3-hydroxy-3-methyl-pentanoate (91g), b.p. 118.5°-123.0° C/0.045mmHg, was obtained.

EXAMPLE 6

β-phenoxyethyl 3-methyl-3-pentenoate (Compound No. 31)

β-phenoxyethyl 3-hydroxy-3-methyl-pentanoate (10g) obtained in Example 5 was refluxed in acetic anhydride (8.8g) for 1 hour and the refluxing was continued for another 5 hours on additon of acetic anhydride (8.8g). Excess acetic anhydride and yielded acetic acid were removed under reduced pressure. The residue was fractionated, giving a fraction, b.p. 124.0°-126.5° C/0.06mmHg, of β-phenoxyethyl 3-methyl-3-pentenoate.

EXAMPLE 7

β-phenoxyethyl 4-bromo-3-methyl-2-butenoate (Compound No. 34)

A solution of bromine (72g) and carbon tetrachloride (500ml) was added dropwise, about 5 hours being required, to the refluxing solution of β-phenoxyethyl 3-methyl-2-pentenoate (99g) [obtained by the same method as described in Example 3 from senecioic acid chloride and β-phenoxy-ethylalcohol] in carbontetrachloride (4l) on illumination of 500W photographic indescent lamp.

The mixture was concentrated under reduced pressure, giving a crude product (128g) [single component by thin layer chromatography (n-hexane:acetone=10:1); infrared absorption spectrum, 1710, 1642, 1600, 1588, 1500, 1240, 1220, 1150, 753 and 690cm$^{-1}$].

Although the fractionation of the title compound was attempted, it failed. Namely, the depressured state suddenly occured under reduced pressure (1.2mmHg) at a elevated temperature (160° C) and the infrared absorption spectrum of the residue was different from the "crude" product. Thin layer chromatography revealed the presence of three new tar-like major components. Therefore this compound, without being refined, was submitted to a biological test. Structure of this "crude" product was identified through syntheses of the derivatives mentioned in Example 8 and 9.

EXAMPLE 8

β-phenoxyethyl 4-acetoxy-3-methyl-2-butenoate (Compound No. 35)

β-phenoxyethyl 4-bromo-3-methyl-2-butenoate (15g) obtained in Example 7 was refluexed with anhydrous sodium acetate (5.32g) in glacial acetic acid (15g) for 8 hours. Ethylether (300ml) and water (20ml) were added to the reaction mixture and the ether layer was washed with water, dried, and concentrated, giving a crude product (11.7g). The crude product on fractionation gave a fractionation gave a fraction (6.1g), b.p. 165°-168° C/0.6mmHg. Structural assignment for this compound was made from its infrared absorption spectrum; 1738, 1710, 1658, 1600, 1590, 1500, 1240, 1215, 1145, 1055, 1040, 755, and 690cm$^{-1}$.

EXAMPLE 9

β-phenoxyethyl 4-methoxy-3-methyl-2-butenoate (Compound No. 36)

β-phenoxyethyl 4-bromo-3-methyl-2-butenoate (15g) obtained in Example 7 was refluxed with calcium carbonate (5g) in methylalcohol (20ml) for 8 days. Methlalcohol was removed under reduced pressure. The residue was poured into water and extracted with ethylether (300ml) and the ether extracts were dried, and concentrated, giving a crude product (10.3g). The crude product on fractionation gave a fraction (4.6g), b.p. 142.0°–143.0° C/0.50mmHg. Structural assignment for this compound was made from its infrared absorption spectrum; 1710, 1650, 1598, 1588, 1495, 1450, 1240, 1212, 1140, 1110, 752, and 690cm$^{-1}$.

EXAMPLE 10

β-phenoxyethyl 3-hydroxy propionate (Compound No. 42)

β-phenoxyethylalcohol (34.5g) was treated with β-propiolacetone (18.0g) at 60°–70° C for 8 hours and then at 90°–100° C for 12 hours. On fractionation, a fraction (20g), b.p. 151.0°–152.0° C/0.07mmHg, of β-phenoxyethyl 3-hydroxy propionate was obtained.

EXAMPLE 11

β-phenoxyethyl pyruvate (Compound No. 43)

This compound was prepared according to a known process (Beilsteins Handbuch der Organischen Chemie, Vol. 3, p616). Namely, the mixture of pyruvic acid (18.6g) and β-phenoxyethylalcohol (27.6g) was heated for 6 hours at 110°–120° C under a reduced pressure (60mmHg) to eliminate water and then fractionated, giving a fraction (15.7g), b.p. 108.0°–109.0° C/0.15mmHg, of β-phenoxyethyl pyruvate.

EXAMPLE 12

β-phenoxyethyl 2-piperidino-3-methyl-2-butenoate (Compound No. 49)

β-phenoxyethyl 2-bromo-3-methyl-2-butenoate (35g) obtained by a known process (Japan Pat. Pub. SHO 49-92232) was dissolved under ice cooling in β-phenoxyethylalcohol (30ml) and piperidine (25g) and then, set aside at room temperature for 4 days. Ethylether (300ml) and benzene (300ml) was added and the organic layer was washed with three 50ml portions of water, dried over Glauber's salt, concentrated under reduced pressure.

The residue, thus obtained, was added to a solution of β-phenoxyethyl alcohol (100ml), benzene (80ml) and sodium (5g) and set aside at room temperature for 24 hours, then benzene (200ml) was added and the benzene layer was washed with water (50ml), dried over Glauber's salt, and concentrated under reduced pressure. A crude product, thus obtained, on fractionation gave a fraction (15.4g), b.p. 128°–130.0° C/0.06mmHg, of β-phenoxyethyl 2-piperidino-3-methyl-2-butenoate.

EXAMPLE 13

β-phenoxyethyl 2-oxo-3-methyl-butanoate (Compound No. 45)

β-phenoxyethyl 2-piperidino-3-methyl-2-butenoate (14g) obtained in Example 12 was added to water (30ml) and concentrated hydrochloric acid (15ml) and then treated at room temperature for 10 hours with vigorous stirring. The reaction mixture was extracted with ethylether (200ml) and benzene (50ml) and the extract was washed with water, dried over Glauber's salt, and concentrated, giving a crude residue (7.2g). The residue on fractionation gave a fraction (5.2g), b.p. 108.5°–109.0° C/0.11mmHg, of β-phenoxyethyl 2-oxo-3-methyl-butanoate.

Example 14

β-phenoxyethyl 3-oxo-butanoate (Compound No. 46)

This compound was prepared according to a known process (Japan Pat. Pub. SHO 27-4873).

Namely, diketene (126g) was added slowly, about one hour being required, under ice cooling to a solution of Sodium (0.75g) in β-phenoxyethylalcohol (414g); ethylether (500ml) was added, washed with water, the ether layer was dried, and concentrated, giving a crude product. The crude product on fractionation gave a fraction (190g), b.p. 125° C/0.18mmHg, of β-phenoxyethyl 3-oxo-butanoate.

EXAMPLE 15

β-phenoxyethyl 3-piperidino 2-butenoate (Compound No. 50)

β-phenoxyethyl 3-oxo-butanoate (16g) obtained in Example 14 and piperidine (6.2g) were allowed to stand for one day under ice cooling and then benzene (100ml) was added and set aside for 2 days at room temperature. Ethyl ether (100ml) was added to the reaction mixture, and the organic layer was washed with water, dried, and concentrated, givng a crude product.

The crude product on fractionation gave a fraction (6g), b.p. 170.0°–185.0° C/0.06mmHg, of β-phenoxyethyl 3-piperidino-2-butenoate.

EXAMPLE 16

β-phenoxyethyl 4-thiomethyl-2-acetyl-butanoate (Compound No. 51)

This compound was prepared according to a known process (Chemical Abstract Vol. 46,3955$^d$). Namely, 2-chloroethyl-methyl thioether (31.2g) was treated with β-phenoxyethyl 3-oxo-butanoate (67.4g), obtained in Example 14, in the solution of β-phenoxyethylalcohol (120ml) and sodium (6.5g) for three hours at 80°–90° C. Benzene (300ml) was added to the reaction mixture and then the organic layer was washed twice with 200ml of water, and concentrated, giving a crude product. The crude product on fractionation gave a fraction (46g), b.p. 160.0° C/0.1mmHg, of β-phenoxyethyl 4-thiomethyl-2-acetyl-butanoate.

EXAMPLE 17

(L)-methionine β-phenoxyethyl-paratoluene sulfonate (Compound No. 55)

The mixture of (L)-methionine (74.6g), paratoluenesulfonic acid (114.1g), β-phenoxyethylalcohol (400g) and benzene (500ml) was refluxed for 5 hours. Benzene was removed under reduced pressure, ethylether (1l) was added and the ether solution was left overnight at room temperature.

Precipitated crystals were filtered and washed four times with 150ml of ethylether. Recrystallized from water (2.8l), from which it yielded colourless crystals (135g), m.p. 122.0°–124.0° C, of (L)-methionine β-phenoxyethyl-paratoluene sulfonate.

EXAMPLE 18

β-phenoxyethyl (L)-N-acetyl-methionate (Compound No. 53)

(L)-methionine β-phenoxyethyl-paratoluene sulfonate obtained in Example 17 was treated with aq. ammonia.

β-phenoxyethyl(L)-methionate (15.2g) thus obtained was disolved in the solution of pyridine (5.2g) and benzene (100ml) and then acetylchloride (4.7g) was added under ice cooling and treated for 4 hours at room temperature. The reaction mixture was washed twice with 100ml of water and the organic layer was dried over Glauber's salt, concentrated under reduced pressure. The concentrate was allowed to stand overnight under cooling. The crystals produced was collected, and washed with 30ml of benzene, giving a colourless crystals (13g), m.p. 59.0°-60.5° C, of β-phenoxyethyl (L)-N-acetyl-methionate.

EXAMPLE 19

β-phenoxyethyl O-acetylglycolate (Compound No. 58)

O-acetylglycolic acid was treated with thionyl chloride and the resulting O-acetylglycollic acid-chloride (41g) was treated with β-phenoxyethyl-alcohol (41.4g) and pyridine (28.4g) in the same way as in Example 3. Thus a fraction (74g), b.p. 117.0°-118.0° C/0.09mmHg, of β-phenoxyethyl O-acetylglycolate was obtained.

EXAMPLE 20

β-phenoxyethyl S-acetylthioglycolate (Compound No. 61)

The solution of potassium hydroxide (6.6g) in water (20 ml) was added under ice cooling to thioacetic acid (7.6g) and then the solution of β-phenoxyethyl bromoacetate (25.9g) in acetone (30ml) was added and treated for 6 hours at room temperature. Extracted twice with 200 ml of ethylether and the ether layer was washed with water, dried, and concentrated, giving colourless crystals (24.9g) which was then recrystallized from n-hexane. Thus colourless crystals (20.8g), m.p. 56.0°-57.0° C, of β-phenoxyethyl S-acetylthioglycolate was obtained.

EXAMPLE 21

β-phenoxyethyl O-methylglycolate (Compound No. 63)

O-methyl glycolic acid chloride (10.9g, b.p. 55° C/95mmHg) obtained by a known process (J. Am Chem. Soc., Vol. 80 p1664, 1958), β-phenoxyethylalcohol (13.8g) and pyridine (9.5g) were treated together with same way as described in Example 1.

On fractionation, a fraction (16g), b.p. 118.0°-120.0° C/0.05mmHg, of β-phenoxyethyl O-methylglycolate was obtained.

EXAMPLE 22

β-phenoxyethyl S-methylglycolate (Compound No. 67)

This compound was prepared according to a known process (Chemical Abstracts Vol. 52, 99442ʰ).

On fractionation, a fraction, b.p. 1200° C/0.1mmHg, of β-phenoxyethyl S-methylglycolate was obtained in a 53% yield.

EXAMPLE 23

β-phenoxyethyl glycolate (Compound No. 68)

Gylcolic acid (22.8g) was dissolved in an aqueous solution of 20% sodium hydroxide (60g) and then trimethylbenzyl ammonium chloride (0.2g), β-phenoxyethyl bromide (50.25g) and n-butylalcohol (200ml) were added and refluxed for 24 hours.

After being washed twice with 100 ml of water, the organic layer was concentrated.

On fractionation, a fraction (4.7g), b.p. 135.0° C/1.0mmHg, of β-phenoxyethyl glycolate was obtained.

EXAMPLE 24

β-phenoxyethyl succinate (Compound No. 70)

β-phenoxyethylalcohol (28g) was treated with succinic acid anhydride (20g) for one hour at 100°-105° C. Precipitated crystals obtained by being kept cool were recrystallized from carbon tetrachloride (300ml), and then recrystallized from carbondisulfide (1l), giving β-phenoxyethyl succinate (31g), m.p. 87.0°-88.0° C.

EXAMPLE 25

β-phenylthioethyl acetate (Compound No. 71)

Acetylchloride (7.9g), β-phenylthioethyl-alcohol (15.4g) and pyridine (9.5g) were treated according to Example 1. On fractionation, a fraction (17.5g), b.p. 76.0°-77.0° C/0.04mmHg, of β-phenylthioethyl acetate was obtained.

EXAMPLE 26

β-phenylthioethyl nitroacetate (Compound No. 78)

This compound was prepared according to a known process (British Pat. No. 835,521 Spec.). Namely, a solution of β-phenylthioethylalcohol (50g) in dichloromethane (15ml) was saturated with dry hydrogen chloride at 0° C. and to the resulting solution was added, in three portions, dipottassium nitroacetate (27.5g). During the addition, hydrogen chloride was passed into the well stirred mixture while the temperature was allowed to rise to 10° C. Then the gas supply was stopped and the reaction mixture was stirred for 4 hours at less than 10° C. After stirring for 20 hours at 0° C., excess β-phenylthioethyl-alcohol was removed under reduced pressure and the remaining solution was kept to cool, the crystals precipitated was washed with water and then with n-hexane, giving β-phenylthioethyl nitroacetate (11.1g), m.p. 22.0°-24.0° C..

EXAMPLE 27

β-phenoxylethyl O-(isopropoxyacetyl-glycolate)

(Compound No. 82)

Isopropoxyacetic acid (b.p. 95.0° C/6mmHg) obtained from isopropyl alcohol, chloroacetic acid and sodium according to Example 21 was treated with thionylchloride, giving isopropoxy acetylchloride. This compound (34.1g) was treated with glycolic acid (19g) according to Example 21, yielding O-(isopropoxyacetyl)glycolic acid (12.0g), b.p. 110.0°-115.0° C/16mmHg. Next, according to Example 1, this compound was treated with β-phenoxyethylalcohol (8g) and pyridine (5.4g). On fractionation, a fraction (10g), b.p. 150°-155.0° C/0.12mmHg, of β-phenoxyethyl O-(isopropoxy-acetyl)-glycolate was obtained.

EXAMPLE 28

β-phenoxyethyl N-chloroacetyl-carbamate
(Compound No. 83)

Chloroacetylisocyanate (12g) was added slowly to the solution of β-phenoxyethylalcohol (13.8g) and benzene (100ml) at room temperature.

The exothermic reaction occured, and the reaction mixture solidified. The solidified mixture was then heated to reflux for 30 minutes to make it a uniformly mixed solution, which was then cooled and the crystals precipitated were collected. β-phenoxyethyl N-chloroacetyl carbamate (22g), m.p. 96.0°–98.0° C, was obtained.

The compounds, i.e. the active ingredients in the present invention, which have been synthesized in the above Examples are listed in Table 1, but they are merely non-restrictive examples of the present invention. The numbers assigned to these compounds are consistently used in the test examples and embodiment examples.

Table 1

| No. | Structure | Physical Properties (b.p. or m.p.) |
|---|---|---|
| 1 | HCOOCH$_2$CH$_2$O—C$_6$H$_5$ | b.p. 85.0 – 87.0° C/1.0 mmHg |
| 2 | CH$_3$COOCH$_2$CH$_2$O—C$_6$H$_5$ | b.p. 88.0 – 89.0° C/0.11 mmHg |
| 3 | CH$_3$CH$_2$COOCH$_2$CH$_2$O—C$_6$H$_5$ | b.p. 92.0° C/0.12 mmHg |
| 4 | CH$_3$(CH$_2$)$_2$COOCH$_2$CH$_2$O—C$_6$H$_5$ | |
| 5 | (CH$_3$)$_2$CHCOOCH$_2$CH$_2$O—C$_6$H$_5$ | b.p. 81.0 – 82.0° C/0.035 mmHg |
| 6 | CH$_3$(CH$_2$)$_3$COOCH$_2$CH$_2$O—C$_6$H$_5$ | b.p. 97.0 – 99.0° C/0.06 mmHg |
| 7 | CH$_3$CH$_2$CH(CH$_3$)COOCH$_2$CH$_2$O—C$_6$H$_5$ | b.p. 88.0 – 90.0° C/0.05 mmHg |
| 8 | (CH$_3$)$_2$CHCH$_2$COOCH$_2$CH$_2$O—C$_6$H$_5$ | b.p. 85 – 86° C/0.1 mmHg |
| 9 | CH$_3$(CH$_2$)$_4$COOCH$_2$CH$_2$O—C$_6$H$_5$ | b.p. 104.0 – 106.0° C/0.05 mmHg |
| 10 | CH$_3$(CH$_2$)$_5$COOCH$_2$CH$_2$O—C$_6$H$_5$ | b.p. 115.0 – 117.0° C/0.07 mmHg |
| 11 | CH$_3$(CH$_2$)$_6$COOCH$_2$CH$_2$O—C$_6$H$_5$ | b.p. 112.0 – 113.0° C/0.05 mmHg |
| 12 | CH$_3$(CH$_2$)$_8$COOCH$_2$CH$_2$O—C$_6$H$_5$ | m.p. 27.5 – 29.0° C (recrystallized from methylalcohol) |
| 13 | CH$_3$(CH$_2$)$_{10}$COOCH$_2$CH$_2$O—C$_6$H$_5$ | m.p. 35.0 – 36.0° C (recrystallized from methylalcohol) |
| 14 | CH$_3$—C(CH$_3$)$_2$—CH$_2$—CH(CH$_3$)—CH$_2$COOCH$_2$CH$_2$O—C$_6$H$_5$ | b.p. 107.5 – 109.5° C/0.045 mmHg |
| 15 | (CH$_3$)$_3$C—COOCH$_2$CH$_2$O—C$_6$H$_5$ | b.p. 102° C/0.3 mmHg |
| 16 | CH$_3$(CH$_2$)$_{11}$COOCH$_2$CH$_2$O—C$_6$H$_5$ | m.p. 39.0 – 41.0° C (recrystallized from methylalcohol) |

Table 1-continued

| No. | Structure | Physical Properties (b.p. or m.p.) |
|---|---|---|
| 17 | CH₃(CH₂)₁₂—COOCH₂CH₂—O—⟨Ph⟩ | m.p. 43.0 – 44.0° C |
| 18 | CH₃(CH₂)₁₃COOCH₂CH₂—O—⟨Ph⟩ | m.p. 45.0 – 47.0° C |
| 19 | CH₃(CH₂)₁₄·COOCH₂CH₂—O—⟨Ph⟩ | m.p. 43.0 – 46.0° C |
| 20 | CH₃(CH₂)₁₅·COOCH₂CH₂—O—⟨Ph⟩ | m.p. 40.0 – 41.0° C |
| 21 | CH₃(CH₂)₁₆·COOCH₂CH₂—O—⟨Ph⟩ | m.p. 50.0 – 52.0° C |
| 22 | CH₃(CH₂)₂₀·COO·CH₂CH₂—O—⟨Ph⟩ | m.p. 57.0 – 59.0° C |
| 23 | CH₂=CH·COOCH₂CH₂—O—⟨Ph⟩ | b.p. 88.0° C/0.1 mmHg |
| 24 | CH₃CH=CH—COOCH₂CH₂O—⟨Ph⟩ | b.p. 96.0° C/0.11 mmHg – 97.0° C/0.12 mmHg |
| 25 | CH₃CH₂—C=CH—COOCH₂CH₂O—⟨Ph⟩, CH₃ | b.p. 104.0 – 105.0° C/0.035 mmHg |
| 26 | (CH₃CH₂)(CH₃CH₂)C=CH—COOCH₂CH₂O—⟨Ph⟩ | b.p. 109.0 – 111.5° C/0.03 mmHg |
| 27 | ⟨H⟩=CH—COOCH₂CH₂O—⟨Ph⟩ | b.p. 142.0 – 146.0° C/0.11 mmHg |
| 28 | (⟨Ph⟩)(⟨Ph⟩)C=CH—COOCH₂CH₂O—⟨Ph⟩ | m.p. 58.0 – 59.0° C |
| 29 | CH₃CH=C(CH₃)—COOCH₂CH₂O—⟨Ph⟩ | b.p. 88.0 – 89.5° C/0.04 mmHg |
| 30 | CH₃C(CH₃)=CHCH₂CH₂·C(CH₃)=CH—COOCH₂CH₂O—⟨Ph⟩ | b.p. 162.0° C/0.11 mmHg – 165.0° C/0.13 mmHg |
| 31 | CH₃CH=C(CH₃)—CH₂—COOCH₂CH₂O—⟨Ph⟩ | b.p. 124.0 – 126.5° C/0.06 mmHg |
| 32 | CH₃CH=C(CH₂CH₃)—CH₂—COOCH₂CH₂O—⟨Ph⟩ | b.p. 124.0° C/0.03 mmHg |
| 33 | ⟨cyclohexyl⟩—CH₂—COOCH₂CH₂O—⟨Ph⟩ | b.p. 147.0 – 149.0° C/0.07 mmHg |
| 34 | BrCH₂—C(CH₃)=CH—COOCH₂CH₂O—⟨Ph⟩ | Decomposed at 160° C |

Table 1-continued

| No. | Structure | Physical Properties (b.p. or m.p.) |
|---|---|---|
| 35 | CH₃COOCH₂C(CH₃)=CH—COOCH₂CH₂O—⟨Ph⟩ | b.p. 165.0 – 168.0° C/0.6 mmHg |
| 36 | CH₃OCH₂C(CH₃)=CH—COOCH₂CH₂O—⟨Ph⟩ | b.p. 142.0 – 143.0° C/0.5 mmHg |
| 37 | CH₃—C(OH)(CH₃)—CH₂—COOCH₂CH₂O—⟨Ph⟩ | b.p. 116.0 – 118.0° C/0.1 mmHg |
| 38 | CH₃CH₂—C(CH₃)(OH)—CH₂—COOCH₂CH₂O—⟨Ph⟩ | b.p. 118.5 – 123.0° C/0.045 mmHg |
| 39 | CH₃CH₂—C(CH₂CH₃)(OH)—CH₂·COOCH₂CH₂O—⟨Ph⟩ | b.p. 131.5° C/0.09 mmHg – 133.5° C/0.095 mmHg |
| 40 | (Ph)₂C(OH)—CH₂·COOCH₂CH₂O—⟨Ph⟩ | m.p. 131.0 – 133.0° C |
| 41 | ⟨cyclohexyl(H)(OH)⟩—CH₂COOCH₂CH₂O—⟨Ph⟩ | b.p. 148.0 – 151.0° C/0.08 mmHg |
| 42 | HOCH₂CH₂COOCH₂CH₂O—⟨Ph⟩ | b.p. 151.0 – 152.0° C/0.07 mmHg |
| 43 | CH₃—C(=O)—COOCH₂CH₂O—⟨Ph⟩ | b.p. 108.0 – 109.0° C/0.15 mmHg |
| 44 | CH₃CH₂—C(=O)—COOCH₂CH₂O—⟨Ph⟩ | b.p. 114.0 – 116.0° C/0.07 mmHg |
| 45 | CH₃—CH(CH₃)—C(=O)—COOCH₂CH₂O—⟨Ph⟩ | b.p. 108.5 – 109.0° C/0.11 mmHg |
| 46 | CH₃—C(=O)—CH₂—COOCH₂CH₂O—⟨Ph⟩ | b.p. 125.0° C/0.18 mmHg |
| 47 | CH₃—C(=O)—CH₂CH₂—COOCH₂CH₂O—⟨Ph⟩ | b.p. 132.0 – 134.0° C/0.07 mmHg |
| 48 | CH₃CH=C(N-piperidinyl)—COOCH₂CH₂O—⟨Ph⟩ | b.p. 149.0 – 158.0° C/0.2 mmHg |
| 49 | CH₃·C(CH₃)=C(N-hexamethyleneimino)—COOCH₂CH₂O—⟨Ph⟩ | b.p. 128.5 – 130.0° C/0.06 mmHg |
| 50 | CH₃·C(N-piperidinyl)=CH—COOCH₂CH₂O—⟨Ph⟩ | b.p. 170.0 – 185.0° C/0.06 mmHg |

Table 1-continued

| No. | Structure | Physical Properties (b.p. or m.p.) |
|---|---|---|
| 51 | CH₃SCH₂CH₂CH(COCH₃)—COOCH₂CH₂O—⟨Ph⟩ | b.p. 160.0° C/0.1 mmHg |
| 52 | CH₃SCH₂CH₂CH(NHCOCH₂O—⟨Ph⟩)—COOCH₂CH₂O—⟨Ph⟩ | m.p. 82.0 – 84.0° C |
| 53 | CH₃SCH₂CH₂CH(NHCOCH₃)—COOCH₂CH₂O—⟨Ph⟩ [L] | m.p. 59.0 – 60.5° C |
| 54 | CH₃SCH₂CH₂CH(NHCOCH₃)—COOCH₂CH₂O—⟨Ph⟩ [DL] | m.p. 64.0 – 66.0° C |
| 55 | (CH₃SCH₂CH₂CH(NH₂)—COOCH₂CH₂O—⟨Ph⟩)·(CH₃—⟨Ph⟩—SO₃H) [L] | m.p. 122.0 – 124.0° C |
| 56 | (CH₃SCH₂CH₂CH(NH₂)—COOCH₂CH₂O—⟨Ph⟩)(CH₃—⟨Ph⟩—SO₃H) [DL] | m.p.133.0 – 135.0° C |
| 57 | (NH₂CH₂COOCH₂CH₂O—⟨Ph⟩)(CH₃—⟨Ph⟩—SO₃H) | m.p. 147.0 – 149.0° C |
| 58 | CH₃COOCH₂COOCH₂CH₂O—⟨Ph⟩ | b.p. 117.0 – 118.0° C/0.09 mmHg |
| 59 | CH₃COOCH(CH₃)COOCH₂CH₂O—⟨Ph⟩ | b.p. 125.0° C/0.17 mmHg |
| 60 | CH₃CH₂COOCH₂COOCH₂CH₂O—⟨Ph⟩ | m.p. 36.0 – 38.0° C |
| 61 | CH₃COSCH₂COOCH₂CH₂O—⟨Ph⟩ | m.p. 56.0 – 57.0° C |
| 62 | CH₃CONHCH₂COOCH₂O—⟨Ph⟩ | m.p. 70.0 – 80.0° C |
| 63 | CH₃OCH₂COOCH₂CH₂O—⟨Ph⟩ | b.p. 118.0 – 120.0° C/0.05 mmHg |
| 64 | CH₃—CH(CH₃)OCH₂COOCH₂CH₂O—⟨Ph⟩ | b.p. 105.0 – 107.0° C/0.14 mmHg |
| 65 | ⟨Ph⟩—CH₂OCH₂COOCH₂CH₂O—⟨Ph⟩ | b.p. 170.0° C/0.21 mmHg |
| 66 | CH₃—C(CH₃)=CH—COOCH₂COOCH₂CH₂O—⟨Ph⟩ | b.p. 145.0 – 146.0° C/0.08 mmHg |
| 67 | CH₃SCH₂COOCH₂CH₂—⟨Ph⟩ | b.p. 120.0° C/0.1 mmHg |
| 68 | HO—CH₂COOCH₂CH₂O—⟨Ph⟩ | b.p. 135.0 C/1.0 mmHg |
| 69 | HOCH(CH₃)COOCH₂CH₂O—⟨Ph⟩ | b.p. 123.0° C/0.8 mmHg |

Table 1-continued

| No. | Structure | Physical Properties (b.p. or m.p.) |
|---|---|---|
| 70 | HOOCCH$_2$CH$_2$COOCH$_2$CH$_2$O—⟨phenyl⟩ | m.p. 87.0 – 88.0° C |
| 71 | CH$_3$COOCH$_2$CH$_2$S—⟨phenyl⟩ | b.p. 76.0 – 77.0° C/0.04 mmHg |
| 72 | CH$_3$OCH$_2$COOCH$_2$CH$_2$S—⟨phenyl⟩ | b.p. 132.0 – 135.0° C/0.05 mmHg |
| 73 | CH$_3$COOCH$_2$COOCH$_2$CH$_2$S—⟨phenyl⟩ | b.p. 131.0 – 132.0° C/0.02 mmHg |
| 74 | CH$_3$—C(CH$_3$)=CHCOOCH$_2$CH$_2$S—⟨phenyl⟩ | b.p. 93.0 – 95.0° C/0.03 mmHg |
| 75 | CH$_3$CONH·CH$_2$CH$_2$S—⟨phenyl⟩ | m.p. 74.0 – 76.0° C |
| 76 | CH$_3$COSCH$_2$CH$_2$O—⟨phenyl⟩ | b.p. 86.0 – 87.5° C/0.1 mmHg |
| 77 | CH$_3$CONHCH$_2$CH$_2$O—⟨phenyl⟩ | m.p. 84.5 – 85.5° C |
| 78 | NO$_2$—CH$_2$COOCH$_2$CH$_2$S—⟨phenyl⟩ | m.p. 22.0 – 24.0° C |
| 79 | CH$_3$CH$_2$COOCH(CH$_3$)—COOCH$_2$CH$_2$O—⟨phenyl⟩ | b.p. 127.0 – 129.0° C/0.12 mmHg |
| 80 | CH$_3$O·CH(CH$_3$)·COOCH$_2$CH$_2$O—⟨phenyl⟩ | b.p. 100.0° C/0.03 mmHg |
| 81 | CH$_3$COOCH$_2$CH$_2$COOCH$_2$CH$_2$O—⟨phenyl⟩ | b.p. 125.0 – 126.0° C/0.05 mmHg |
| 82 | CH$_3$CHOCH$_2$COCH$_2$COOCH$_2$CH$_2$O—⟨phenyl⟩ (with CH$_3$ and O substituents) | b.p. 150.0 – 155.0° C/0.12 mmHg |
| 83 | Cl·CH$_2$CONHCOO—CH$_2$CH$_2$O—⟨phenyl⟩ | m.p. 96.0 – 98.0° C |

Note: (L) and (DL) in Table 1 mean respectively that L-amino acid has been used as starting material and DL-amino acid has been used as starting material.

Most of the compounds listed in Table 1 are novel ones not yet mentioned in any literature, but some of them are known to have very low toxicity to animals.

For example, John H. Draize et al. and Geoffrey Woodard et al. reported in J. Pharmacol. & Exptl. Therap. Vol. 93, PP 26–39, 1948 that the compound No. 2 showed a low value of acute oral toxicity to rats, i.e., LD$_{50}$ 4900 mg/Kg; and was not likely to cause skin cancer; and thus it was a highly safe chemical to animals. The other compounds, according to the results of preliminary tests (on acute oral toxicity to mice) carried out by the present inventors, showed invariably an LD$_{50}$ value of more than 1000 mg/Kg and thus they were found low in toxicity. Meanwhile, J. P. Linduska, J. H. Cochran and F. A. Morton reported in J. of Econ. Entomol. Vol. 39, PP 767-9 (1946) and B. V. Travis and Carroll N. Smith in the same journal Vol. 44, PP 428-9 (1951) reported that the compound No. 2 was feebly repellant to pests like fleas, mosquitoes etc. According to the French Pat. No. 1,499,228 granted to Roussos, Michel, Bourgeois, Yves and Jasse, Bruno, the compound No. 5 and the like can be applied as an additive to PVC.

Meanwhile, the compound No. 5 has been tested as a bactericide. Thus Jasper C. Maruzzella and Eugene Bramnick stated in Soap, Perfumery and Cosmetics, Vol. 34, PP 743-5 (1961) that the compound No. 5 even in a high concentration of 2000 ppm had proved nonbactericidal to genus Bacillus, *Escherichia coli* and *Micrococcus pyogenes* var. *aureus*.

With regard to some of the compounds listed in Table 1, the present inventors have carried out fungicidal tests on Fusarium, which is a typical soil fungi, using a agar dilution method and thereby confirmed that these compounds are very feebly fungicidal. Pot tests, however, of such hardly fungicidal compounds of this invention showed an interesting result that these compounds in such a low concentration that cannot be expected to be effective from the results of fungicidal test by agar dilution method can be extremely effective for preventing damage due to Fusarium. The following are references and tests showing details of this invention.

Reference — Fungicidal Test by Agar Dilution Method 100 mg of the invented compound was taken in a 30 ml conical flask, to which a drop of 1:1 mixture of Solpol 2680 (surface-active agent produced by Toho Kagaku) and xylene (about 25 mg), and 1 ml of acetone were added to dissolve therein. On the other hand, 9 ml of sterilized water separately was further added to emulsify, thereby yielding an emulsion of 10,000 ppm concentration. From this emulsion of 5,000 ppm and one of 2,500 ppm were prepared through two times dilution.

In a 100 ml conical flask, 3 ml portion each of these emulsions was taken; 27 ml of potato-sucrose-agar (PSA) medium, at 50°-60° C was added and uniformly blended. Ten ml of the obtained mixture was poured and hardened on a 10 cm-diameter petri dish.

Meanwhile, a colony of *Fusarium oxysporum* f. *cucumerinum* separately cultivated on potato-sucrose-agar (PSA) medium was stamped out by a 4mm-diameter cork-borer and inoculated on the above-mentioned mixed medium. After 4 days of cultivation in a chamber of 25° C, the diameter of the colony was measured, the results being summarized in Table 2. A case of the colony not having grown is indicated by the sign (-).

Table 2

| Invented Compounds | Inhibitive effect-confirmation test by agar dilution method | | |
|---|---|---|---|
| | Concentration (ppm) | | |
| No. | 250 | 500 | 1000 |
| 1 | 40 mm | 30 mm | 10 mm |
| 2 | 37 | 26 | — |
| 3 | 25 | 20 | 9 |
| 4 | 32 | 27 | 22 |
| 5 | 30 | 23 | 17 |
| 6 | 31 | 26 | 22 |
| 7 | 25 | 23 | 16 |
| 8 | 24 | 19 | 15 |
| 9 | 33 | 30 | 22 |
| 10 | 33 | 28 | 24 |
| 11 | 36 | 32 | 29 |
| 12 | 46 | 41 | 38 |
| 13 | 49 | 45 | 40 |
| 14 | 38 | 38 | 35 |
| 15 | 19 | 17 | 13 |
| Control | 45 | 42 | 39 |
| 50% wettable power of Benomyl | — | — | — |
| | (2.5ppm) | (5ppm) | (10ppm) |

Note * control medium is a mixed medium containing only Solpol and acetone in the same amounts as the treated lot.
** Benomyl: the effective ingredient is methyl-1-(butylcarbamonyl)-2-benzimidazol-carbamate.

As seen from Table 2, the invented compounds No. 12 and No. 13 have the same growth as the control, while the others of the invented compounds are only slightly more inhibitive than the control. In the case of Benomyl, which is 2.5, 5 and 10 ppm in concentration, that is 1/100 of the concentration used in the testing of invented compounds, no growth of the colony was evident, testifying to high inhibitive effect.

Test 1

Test of effect of fungicide on control of Fusarium wilt of cucumber (in case of using powder)

*Fusarium oxysporum* f. *cucumerinum* which had been cultivated for 1 month at 25° C on soil-bran medium was air-dried overnight and sifted through a 3mm-mesh sieve. 10g of said culture soil was blended with 600g of sterilized diluvial soil. To 200g of this blended soil were added 1200g of sterilized diluvial soil (containing 2.65 weight % of compost) and 1000mg or 500mg of 5% powder of the invented compound; and these were uniformly mixed in a vat. Next, 1500g of sterilized diluvial soil (containing compost) was placed in a wagner pot of 1/5000 are over which was spread the soil prepared above. Cucumber seedlings of one-leaf stage (variety: "Shimoshirazujibai") which had been cultivated separately in styrol cups in a greenhouse were transplanted into said wagner pot. Each of said cucmber seedlings was singly planted in 200g of the soil placed in said styrol cup and three days before its transplanting, 20 ml of an emulsion of each compound in 300 ppm concentration was irrigated over the soil. In the case of a pot whose soil had been treated with 1000 mg of the compound (5% powder), 14 days after transplanting, 50 ml of an emulsion of the compound in 1000 ppm concentration was additionally irrigated (Test I) and in the case of a pot whose soil had been treated with 500mg of the compound (5% powder), 50 ml of an emulsion of the compound in 500 ppm concentration was additionally irrigated (Test II). The pots were all kept in a greenhouse, and the test was carried out on lots each containing three pots, each pot holding four seedlings.

Every 2 days the withered seedlings were counted and in the fourth week of transplanting, the browning degree of vascular in each seedling was measured; and the effectiveness rating was determined as follows;

Effectiveness rating = $(1 - \frac{\text{sick score of each treated lot}}{\text{sick score of Fusarium lot*}}) \times 100$ (Note)*Fusarium lot is a treated lot containing only *Fusarium oxysporum* f. *cucumerinum*.

Sick score is obtained as follows:

Sick score = $3 \times a + 2 \times b + 1 \times c + 0.5 \times d + 0 \times e$ where
a — number of withered seedlings
b — number of seedlings in which the browning of vascular has reached the cotyledon part
c — number of seedlings in which the browning of vascular is short of the cotyledon part
d — number of seedlings in which only brown spots have been recognized
e — number of perfectly sound seedlings $a + b + c + d + e = 12$ The results are summarized in Table 3.

Table 3

| Invented Compound | Test of effect of fungicide on control of Fusarium wilt of cucumber | |
|---|---|---|
| | Effectiveness Rating | |
| No. | I* | II** |
| 1 | 62 | — |
| 2 | 82 | 80 |
| 3 | 67 | 32 |
| 4 | 76 | 30 |
| 5 | 72 | — |
| 6 | 68 | — |
| 7 | 77 | — |
| 8 | 91 | 50 |
| 9 | 67 | — |
| 10 | 60 | — |
| 11 | 68 | — |
| 12 | 77 | — |

Table 3-continued

Test of effect of fungicide on control of Fusarium wilt of cucumber

| Invented Compound No. | Effectiveness Rating I* | II** |
|---|---|---|
| 13 | 68 | — |
| 14 | 75 | — |
| 15 | 72 | — |
| 16 | 68 | — |
| Benomyl | 70 | 44 |

Note:
*I is the case in which soil treatment and additional irrigated with compound were done with 1000mg (5% powder) and 1000 ppm.
**II is the case in which soil treatment and additional irrigated with compound were done with 500mg (5% powder) and 500 ppm.

From Table 3 it is apparent that the invented compounds are as effective as Benomyl. In the reference, that is inhibitive effect-confirmation test by agar dilution method, the compounds according to the present invention, even in over 100 times as heavy concentration as Benomyl, turned out very feebly effective, but in Test 1, i.e., practical test of effect of fungicide on control of Fusarium wilt of cucumber they proved as effective as Benomyl in the same concentration as the latter. From this fact it is surmised that the compounds of the present invention are weak in fungicidal power but strongly effective for protecting the crop.

Test 2

Test of effect of fungicide on control of Fusarium wilt of cucumber (in case of using emulsion).

*Fusarium oxysporum* f. *cucumerinum* which had been cultivated for 1 month at 25° C on soil-bran medium was air-dried overnight and then sifted through a 3 mm-mesh sieve. 15g of said culture soil and 600g of sterilized diluvial soil were blended together. 1200g of sterilized diluvial soil (containing 2.65 weight % of compost) was added to 200g of the blended soil and uniformly mixed in a vat.

Next, 1500g of sterilized diluvial soil (containing compost) was placed in a Wagner pot of 1/5000 are, over which the soil prepared above was spread. Cucumber seedlings of one-leaf stage (variety: "Shimo-shirazujibai") which had been separately cultivated in styrol cups in a greenhouse were transplanted into said Wagner pot. Each of said cucumber seedlings was singly grown in a styrol cup with 200g of soil. Seven days before it was transplanted, 20 ml of an emulsion of each compound in 300 ppm was irrigated over the soil. Just after transplanting and two weeks after transplanting 50 ml of an emulsion of the compound in 1000 ppm was additionally irrigated. All pots were kept in the greenhouse, the test being carried out on lots each containing three pots and each pot holding four seedlings.

In the third week of transplanting all the seedlings were checked for the browning degree of vascular and in the same way as in Test 1, the effectiveness rating and the sick score were determined. The results are summarized in Table 4.

Table 4

| Invented Compounds No. | Effectiveness Rating | Invented Compounds No. | Effectiveness Rating |
|---|---|---|---|
| 17 | 59 | 50 | 23 |
| 18 | 55 | 51 | 55 |
| 19 | 58 | 52 | 60 |
| 20 | 48 | 53 | 75 |
| 21 | 36 | 54 | 78 |
| 22 | 59 | 55 | 78 |
| 23 | 68 | 56 | 60 |
| 24 | 59 | 57 | 35 |
| 25 | 68 | 58 | 65 |
| 26 | 51 | 59 | 57 |
| 27 | 23 | 60 | 69 |
| 28 | 23 | 61 | 53 |
| 29 | 61 | 62 | 35 |
| 30 | 30 | 63 | 78 |
| 31 | 32 | 64 | 66 |
| 32 | 30 | 65 | 73 |
| 33 | 49 | 66 | 40 |
| 34 | 64 | 67 | 89 |
| 35 | 56 | 68 | 78 |
| 36 | 60 | 69 | 60 |
| 37 | 53 | 70 | 45 |
| 38 | 45 | 71 | 70 |
| 39 | 53 | 72 | 79 |
| 40 | 23 | 73 | 64 |
| 41 | 34 | 74 | 43 |
| 42 | 63 | 75 | 44 |
| 43 | 60 | 76 | 40 |
| 44 | 60 | 77 | 40 |
| 45 | 59 | 78 | 21.5 |
| 46 | 50 | 79 | 72 |
| 47 | 50 | 80 | 65 |
| 48 | 23 | 81 | 68 |
| 49 | 23 | 82 | 66 |
|  |  | 83 | 70 |

Test 3

Test of effect of fungicide on control of Fusarium wilt of tomato

*Fusarium oxysporum* f. *lycopersici* which had been cultivated for 1 month at 25° C on soil-bran medium was air-dried overnight and then sifted through a 3mm-mesh sieve. 15 g of said culture soil and 600 g of sterilized diluvial soil were blended together. 200 g of the blended soil was added to 1200 g of sterilized diluvial soil (containing 2.65 weight % of compost) and uniformly mixed in a vat.

Next, 1500 g of sterilized diluvial soil (containing compost) was placed in a wagner pot of 1/5000 are, over which the soil prepared above was spread. Tomato seedlings of one-leaf stage (variety: "Hikari") which had been separately grown in styrol cups in a greenhouse were transplanted into said Wagner pot. Each of said tomato seedlings was singly grown in a styrol cup with 200 g of soil, and 7 days before it was transplanted, 20 ml of an emulsion of the compound in 300 ppm was irrigated into the soil.

Just after transplanting and two weeks after transplanting, 50 ml of an emulsion of the compound in 100 ppm was additionally irrigated. All the pots were kept in the greenhouse, the test being carried out on lots each containing three pots with each pot holding four seedlings.

In the third week of transplanting, all seedlings were checked for the browning degree of and in the same way as in Test 1, the effectiveness rating and the sick score were determined, the results being summarized in Table 5.

Test 4

Test of effect of fungicide on control of yellows of radish

*Fusarium oxysporum* f. *raphani* which had been cultivated for 1 month at 25° C on soil-bran medium was air-dried overnight and then sifted through a 3mm-mesh sieve. 3 g of said culture soil and 600 g of sterilized diluvial soil was flended together. 200 g of the blended soil was added to 1200 g of sterilized diluvial soil (containing 2.65 weight % of compost) and 170 mg of a 25% wettable powder of an invented compound, and mixed uniformly in a vat.

Next, 1500 g of sterilized diluvial soil (containing compost) was placed in a Wagner pot of 1/5000a, over which the soil prepared above was spread; and at 5-10 mm depth from the top layer three seeds of radish (variety: "Miyako") were sown. Twenty-one days after sowing, a 1000 ppm solution of 25% wettable powder of an invented compound was irrigated at a rate of 50 ml per pot. The pots were kept in a greenhouse and the test was carried out on lots each containing 4 pots with each pot holding three seedlings.

In the sixth week of sowing, all the seedlings were checked for the browning degree of and in the same way as in Test 1 the effectiveness rating and the sick score were determined, the results being summarized in Table 5.

Test 5

Test of effect of fungicide on control of yellows of cabbage

*Fusarium oxysporum* f. *conglutinans* was treated in the same way as in Test 3 and cabbage (variety: "Koetsu") was used as the test crop; otherwise the test was done in the same way as Test 4. The results are summarized in Table 5.

Table 5

Results of tests of effect of fungicide on control of Fusarium wilt of tomato, yellows of radish and yellows of cabbage

| Invented Compounds No. | Effectiveness Rating | | |
|---|---|---|---|
|  | Tomato | Cabbage | Radish |
| 2 | 46 | 85 | 59 |
| 13 | 50 | 55 | 53 |
| 37 | 50 | 62 | 67 |
| 45 | 50 | 52 | 53 |
| 51 | 54 | 68 | 44 |
| 58 | 54 | 62 | 53 |
| 68 | 42 | 55 | 44 |
| 71 | 58 | 55 | 92 |
| 76 | 48 | 46 | 41 |
| 77 | 38 | 55 | 36 |

Test 6

Test of effect of fungicide on control of Fusarium wilt of cucumber, by spraying stalks and leaves with compound.

*Fusarium oxysporum* f. *cucumerinum* which had been cultivated for 1 month at 25° C on soil-bran medium was air-dried overnight and then sifted through a 3mm-mesh sieve. 15 g of said culture soil and 1200 g of sterilized diluvial soil (containing 2.65 weight % of compost) were blended together uniformly in a vat.

Next, 1500 g of sterilized diluvial soil (containing compost) was placed in a Wagner pot of 1/5000a, over which the soil prepared above was spread. Cucumber seedlings of one-leaf stage (variety: "Shimoshiraznjibai") which had been separately grown in styrol cups in a greenhouse were transplanted into said Wagner pot. Each of said cucumber seedlings was singly grown in a styrol cup with 200 g of soil. Seven days before it was transplanted, it was sprayed with a 2000 ppm solution of each compound until the stalks and leaves were completely wet.

Just after transplanting and at the end of each week after transplanting, the seedling was sprinkled until completely wet with a 2000 ppm solution of the compound. All the pots were kept in the greenhouse. The test was carried out on lots of three pots each with each pot holding four seedlings.

In the third week of transplanting all the seedlings were checked for the browning of vascular and in the same way as in Test 1. The effectiveness rating and the sick score were determined and the results were summarized in Table 6.

Table 6

Results of effect of fungicide on control of Fusarium wilt of cucumber by sprayed of stalks and leaves.

| Invented Compounds No. | Effectiveness Rating 2000 ppm |
|---|---|
| 2 | 67 |
| 23 | 30 |
| 37 | 40 |
| 45 | 76 |
| 74 | 62 |

The following are some examples of embodying the present invention, the parts indicated being weight parts.

| Example 1 - Wettable powder | |
|---|---|
| Invented compound No. 42 | 27 parts |
| Zeeklite PFP,(filler produced by Zeeklite Kogyo | 16 parts |
| Solpol 5039 (emulsifier produced by Toho Kagaku | 4 parts |
| Carplex (filler produced by Shionogi Seiyaku | 20 parts |
| Lignin | 3 parts |
| Diatom earth (Trade name) | 30 parts |

The above items were uniformly crushed and blended into a wettable powder.

| Example 2 - Emulsion | |
|---|---|
| Invented compound No. 55 | 50 parts |
| Xylene | 37.5 parts |
| Solpol 2680 (emulsifier produced by Toho Kagaku | 12.5 parts |

The above items were mixed and dissolved into an emulsion.

| Example 3 - Powder | |
|---|---|
| Invented compound No. 2 | 5 parts |
| Carplex (anti-hardening agent) produced by Shionogi Seiyaku | 3 parts |
| Newlex powder (surface active agent produced by Nihon Yushi) | 1 part |
| Clay | 81 parts |

The above items were uniformly crushed and blended into a powder.

What is claimed is:

1. A method of protecting a plant or a crop from damage due to soil fungi which comprises applying to the soil or to the crop plants a fungicidally effective amount of at least one of the followng compounds having the general formula:

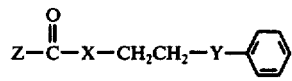

wherein Z is selected from the group consisting of hydrogen, alkyl containing 1 to 21 carbon atoms and alkenyl containing 2 to 6 carbon atoms and both X and Y are oxygen.

2. The method of claim 1, in which Z is an alkyl group which contains 1-21 carbon atoms.

3. The method of claim 1, wherein said soil fungi are Fusarium fungi.

4. The method of claim 1, wherein said compound is applied to the soil at a rate of from 30 grams to 250 grams per are.

5. The method of claim 1, wherein said compound is applied to crop plants at a rate of from 1,000 to 2,000 ppm and the crop plants are sufficiently wetted.

6. The method of claim 1, wherein said compound is β-phenoxyethyl acetate having the formula:

7. The method of claim 1, wherein said compound is β-phenoxyethyl laurate having the general formula:

8. A method of inhibiting soil fungi by treating the soil with the composition used in claim 1.

* * * * *